United States Patent [19]

Miller

[11] Patent Number: 4,944,876
[45] Date of Patent: Jul. 31, 1990

[54] FILTER CAPSULE WITH INLET DISPERSION

[75] Inventor: Michael R. Miller, Churubusco, Ind.

[73] Assignee: Telectro-Mek, Inc., Fort Wayne, Ind.

[21] Appl. No.: 416,714

[22] Filed: Oct. 3, 1989

[51] Int. Cl.$^5$ .............................................. B01D 61/18
[52] U.S. Cl. ........................... 210/321.75; 210/321.84; 210/446; 210/450; 210/451; 210/455; 210/456
[58] Field of Search ............... 210/634, 641, 644–647, 210/649–654, 321.6, 321.62, 321.64, 321.75, 321.84, 406, 416.1, 416.4, 418–420, 428, 435, 445, 446, 450, 451, 453, 455, 456, 459

[56] References Cited

U.S. PATENT DOCUMENTS

| | | |
|---|---|---|
| 1,496,771 | 6/1924 | Cash . |
| 1,595,983 | 8/1926 | Armstrong . |
| 2,073,991 | 3/1937 | Koser . |
| 2,665,009 | 1/1954 | Harstick . |
| 2,754,005 | 7/1956 | Tursky . |
| 2,784,843 | 3/1957 | Braunlich . |
| 3,360,131 | 12/1967 | Witkowaki . |
| 3,373,875 | 3/1968 | Krikorian . |
| 4,170,056 | 10/1979 | Meyst et al. . |

Primary Examiner—Frank Sever
Attorney, Agent, or Firm—Jeffers, Hoffman & Niewyk

[57] ABSTRACT

A fuel monitor assembly for use in testing the contamination level of a fuel sample is disclosed, including a housing having a fuel inlet and a fuel outlet, and a fuel filter capsule disposed within the housing. The filter capsule includes an inlet half and an outlet half, wherein the halves interfit to retain a membrane filter therebetween. The inlet half of the filter capsule is integrally formed with an inlet dispersion structure that radially disperses an incoming stream of fuel so as to equalize the pressure across the face of the membrane filter, thereby resulting in even distribution of contaminant particulates deposited on the membrane filter. The outlet half of the filter capsule is integrally formed with a recessed, radially symmetric grid configuration that channels fuel passing through the membrane filter to the fuel outlet, and also encourages equal pressure distribution across the face of the membrane filter.

20 Claims, 1 Drawing Sheet

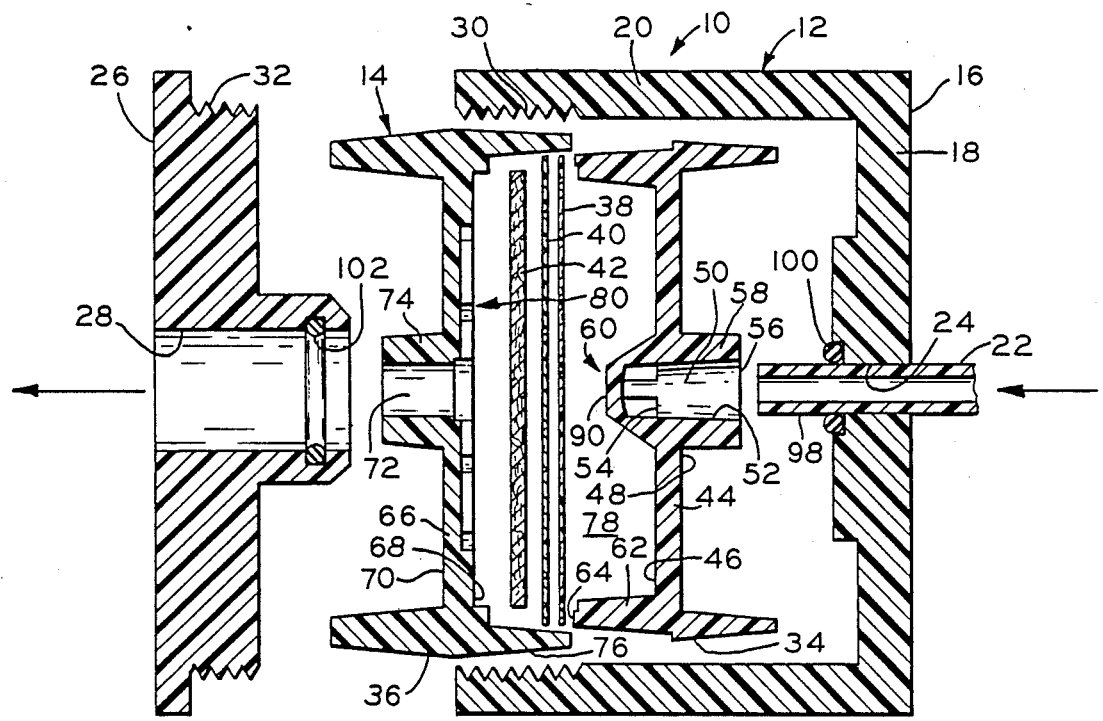
FIG. 1
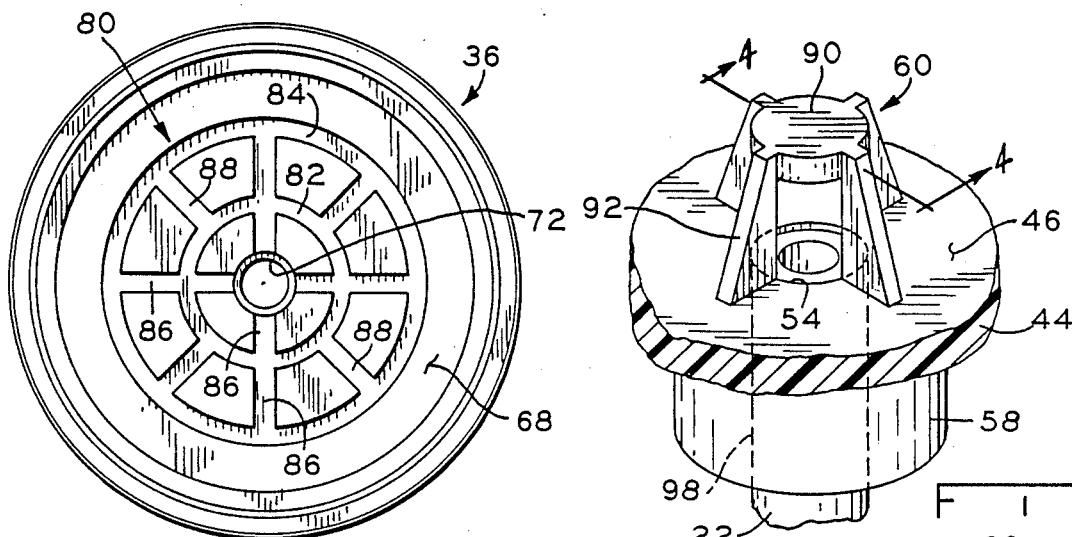
FIG. 2
FIG. 3
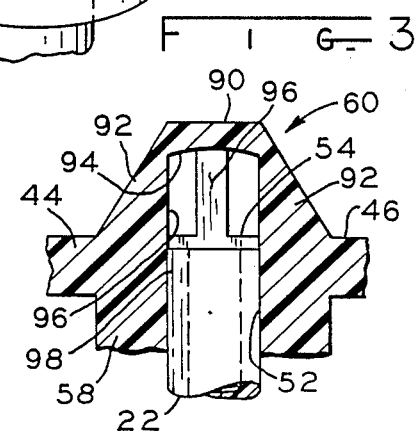
FIG. 4

FILTER CAPSULE WITH INLET DISPERSION

BACKGROUND OF THE INVENTION

The present invention relates generally to particulate detection systems for determining particulate levels in fluid samples. More specifically, the present invention relates to such systems that utilize filter assemblies, wherein a membrane filter is retained within a filter capsule having an inlet and an outlet to permit fluid to pass through the filter and deposit suspended particulates thereon for further analysis.

A variety of particulate detection systems are currently used in laboratories and in field operations to determine particulate concentrations in various fluid testing applications. For example, an important application for a particulate detection system is the testing of aircraft fuel supplies for unacceptable levels of particulate contamination. Many of the detection systems currently in use are based upon one of several conventional techniques utilizing a membrane filter on which particulates are deposited. The membrane filter is analyzed to determine the amount of particulates on the filter, thereby indicating the concentration of particulates in the fluid sample. The most common methods currently used to analyze the membrane filter are Gravimetric Assessment, Colormetric Assessment, or Visual Assessment.

The Gravimetric Assessment method of analyzing the membrane filter involves actual weighing of the particulate products retained on the membrane filter after the fluid has been passed therethrough. The Colormetric Assessment method involves evaluating the particulate laden membrane filter on the basis of coloration, hue, chroma, and intensity. The Visual Assessment method relies upon a skilled operator to correctly identify the quality and quantity of particulates deposited on the membrane filter.

As previously noted, particulate detection systems are used in field testing of aircraft fuel supplies. One such fuel testing system is the Accumetric fuel contamination detector, manufactured by TMI of Fort Wayne, Ind., which utilizes the principle of differential light transmission through membrane filters to measure particulate contamination levels. More specifically, two membrane filters are used in series, wherein the first filter traps particulates and acquires fuel coloration while the second filter acquires only fuel coloration. The Accumetric fuel contamination detector processes differential readings from the filters, automatically compensates for fuel coloration, and indicates a particulate contamination level.

In each of the aforementioned methods of analyzing a membrane filter to determine the particulate count, the accuracy of the measurement is affected by uneven particulate distribution on the sample filter. One primary cause of such uneven particulate distribution is the design limitations of the sampling equipment used to house the membrane filter. A typical monitor capsule used in fuel sampling includes an inlet half having a centrally located inlet port, an outlet half having a centrally located outlet port, and a membrane filter retained between the halves, through which liquid fuel is passed. According to this conventional design, a stream of fluid enters the inlet port and impacts directly against a central portion of the membrane filter face. Consequently, the fluid pressure across the filter face varies greatly, resulting in a "halo" of concentrated particulates at the outer periphery and a "hole" of relatively clean filter area in the center of the filter face.

The present invention is directed to overcoming the aforementioned problems associated with prior art filter assemblies for particulate detection systems, wherein it is desired to provide an improved membrane filter capsule that is capable of providing substantially uniform fluid pressure distribution across the face of the membrane filter, thereby resulting in even particulate distribution and improved accuracy of the associated particulate detection system.

SUMMARY OF THE INVENTION

The present invention overcomes the problems and disadvantages of the above-described prior filter assemblies by providing an improved membrane filter capsule for particulate detection systems, wherein a fluid sample entering the inlet of the filter capsule is radially dispersed to provide substantially uniform fluid pressure distribution across the face of the membrane filter, thereby improving the distribution of particulates on the membrane filter for subsequent analysis.

Generally, the present invention provides a filter capsule assembly including an inlet half having an inlet opening, and an outlet half having an outlet opening. The two halves engage one another to define a filter chamber in which a membrane filter is disposed such that a fluid sample entering the inlet opening passes through the filter and exits through the outlet opening. The inlet half is formed with a fluid dispersion structure that acts to radially disperse the incoming stream of fluid so that it does not directly impact the membrane filter. Consequently, the fluid pressure is uniformly distributed across the face of the membrane filter.

More specifically, the present invention provides, in one form thereof, a filter capsule assembly including a molded plastic inlet half having a bottom surface and a fluid inlet opening extending therethrough along a longitudinal axis normal to the bottom surface. A planar filter element is retained intermediate the inlet half and a corresponding outlet half in a plane generally parallel to the bottom surface and transverse to the longitudinal axis. A fluid dispersing structure is integrally molded with the inlet half, and functions to radially disperse a stream of fluid that would enter through the fluid inlet opening. The fluid dispersing structure includes a fluid-contacting plate that is supported above the bottom surface in registry with the fluid inlet opening. The fluid-contacting surface of the fluid-contacting plate has an area no greater than the minimum cross-sectional area of the fluid inlet opening along the axial length thereof.

An advantage of the filter capsule of the present invention is that particulates from a fluid sample passed through the capsule are evenly distributed on the face of the membrane filter, thereby facilitating subsequent analysis of the filter.

A further advantage of the filter capsule of the present invention is that fluid pressure across the face of the membrane filter is uniformly distributed, thereby enabling uniform deposition of particulates onto the filter.

Yet another advantage of the filter capsule of the present invention is that an incoming stream of fluid is radially dispersed, thereby protecting the membrane filter against direct impact from the fluid and facilitating "washing" of the peripheral edge of the filter membrane where particulates would otherwise concentrate.

A still further advantage of the filter capsule of the present invention is that a uniform distribution of particulates on the filter membrane is achieved despite variances in the line pressure of the incoming fluid sample, thereby improving testing accuracy and repeatability under various fluid sampling conditions.

Another advantage of the filter capsule of the present invention, in one form thereof, is that it is easily manufactured by a molding process without inserts and the like.

The invention, in one form thereof, provides a filter capsule assembly through which a fluid sample is passed in order to filter off particulates suspended therein, wherein the particulates are subsequently analyzed to determine the particulate contamination level of the fluid sample. The filter capsule includes an inlet half and an outlet half. The inlet half includes an inlet bottom wall, a fluid inlet opening extending through the inlet bottom wall, and an inlet side wall extending upwardly from the inlet bottom wall. The fluid inlet opening extends along a longitudinal axis substantially normal to the inlet bottom wall, and has along the axial length thereof a minimum transverse cross-sectional area. The outlet half includes an outlet bottom wall, a fluid outlet opening extending through the outlet bottom wall, and a generally cylindrical outlet side wall extending upwardly from the outlet bottom wall. The inlet half and the outlet half are adapted to engage one another to define a filter chamber bounded by the inlet and outlet bottom walls and the inlet and outlet side walls. A filter element is retained intermediate the inlet bottom wall and the outlet bottom wall within the filter chamber when the inlet half and the outlet half are engaged. A fluid dispersion structure is associated with the inlet half for radially dispersing a stream of fluid that would enter the filter chamber through the fluid inlet along the longitudinal axis. The fluid dispersion structure includes a fluid-contacting plate member and support members extending between the inlet bottom wall and the peripheral edge of the plate member for supporting the plate member in spaced relationship with the inlet bottom wall. The plate member has a fluid-contacting surface facing the inlet bottom wall in registry with the fluid inlet opening along the longitudinal axis. The area of the fluid-contacting surface is no greater than the minimum transverse cross-sectional area of the fluid inlet opening.

BRIEF DESCRIPTION OF THE DRAWINGS

FIG. 1 is an exploded sectional view of a fuel monitor assembly of the type to which the present invention pertains, including a fuel filter capsule in accordance with the present invention;

FIG. 2 is a plan view of the filter support side of the outlet half of the fuel filter capsule of FIG. 1, particularly showing a radially symmetric grid pattern formed therein;

FIG. 3 is an enlarged perspective view of fuel dispersion means associated with the inlet half of the fuel filter capsule of FIG. 1, in accordance with a preferred embodiment of the present invention; and FIG. 4 is a fragmentary sectional view of the fuel dispersion means of FIG. 3, taken along the line 4—4 in FIG. 3 and viewed in the direction of the arrow.

DESCRIPTION OF THE PREFERRED EMBODIMENT

In an exemplary embodiment of the invention as shown in the drawings, and in particular by referring to FIG. 1, there is shown a fuel monitor assembly 10, including an aluminum outer enclosure assembly 12 and a filter capsule assembly 14 housed therein. Enclosure 12 includes a cup-shaped inlet member 16 having a bottom wall 18 and a cylindrical side wall 20. A stainless steel fluid inlet pipe 22 extends through an axial bore 24 located in the center of bottom wall 18. Enclosure 12 also includes a lid member 26 having a centrally located fluid outlet port 28 formed therein, which is in axial alignment with axial bore 24 when lid member 26 is engaged with inlet member 16 by means of internal threads 30 on side wall 18 and external threads 32 on the periphery of lid member 26. In a preferred embodiment of the invention, outer enclosure assembly 12 consists of either a Mini-Monitor fuel sampling assembly, commercially available from Gammon Technical Products of Masaquan, N.J. or a Millipore fluid sampling kit, commercially available from Millipore Corporation of Bedford, Mass.

In accordance with a preferred embodiment of the present invention, filter capsule assembly 12 includes an inlet half 34, an outlet half 36, a pair of membrane filters 38 and 40, and a filter support pad 42. Inlet half 34 is a molded cup-shaped piece, including a planar bottom wall 44 having an inside surface 46 and an outside surface 48. An axial fluid inlet passage 50 extends through bottom wall 44 at a central location thereof. More specifically, inlet passage 50 is defined by an inner surface 52 that is symmetric about a central longitudinal axis normal to planar bottom wall 44. Inner surface 52 extends from an opening 54 on inside surface 46 to an opening 56 at the distal end of a boss 58 extending axially from outside surface 48. In accordance with the present invention, fluid entering inlet passage 50 will encounter a fluid dispersion structure 60, which will be more fully described hereinafter.

With continued reference to inlet half 34, a cylindrical side wall 62 extends upwardly from the outer peripheral edge of bottom wall 44, thereby defining a cup-shaped structure for inlet half 34. Side wall 62 is coaxial with the aforementioned longitudinal axis of inlet passage 50, and includes an axially inwardly facing annular top edge 64.

Outlet half 36 is preferably a molded cup-shaped piece, including a bottom wall 66 having an inside surface 68 and an outside surface 70. An axial fluid outlet 72 passage extends through bottom wall 66 at a central location thereof. More specifically, outlet passage 72 extends through bottom wall 66 and a boss 74 extending axially from outside surface 70. A cylindrical side wall 76 extends upwardly from bottom wall 66, thereby defining a cup-shaped structure for outlet half 36 similar to that of inlet half 34. As graphically illustrated by the exploded view of FIG. 1, side wall 62 is adapted to be frictionally telescopingly received within side wall 76. Accordingly, upon engagement of inlet half 34 with outlet half 36, respective bottom walls 46 and 66 face one another in spaced relationship and define a filter chamber 78 therebetween circumferentially bounded by side walls 62 and 76.

Membrane filters 38 and 40 and support pad 42 are disposed within filter chamber 78 in a plane transverse to the aforementioned longitudinal axis of inlet passage 50. In the disclosed preferred embodiment, membrane filters 38 and 40 and support pad 42 are retained adjacent inside surface 68 of bottom wall 66 when inlet half 34 and outlet half 36 are selectively engaged. More specifically, the outer peripheral edges of membrane filters 38 and 40 are retained intermediate annular top edge 64 and bottom wall 66. In accordance with the preferred embodiment, membrane filters 38 and 40 are Millipore membrane filters, as manufactured by Millipore Corporation of Bedford, Mass. measuring 0.8 microns in nominal aperture and 37.0 millimeters in diameter.

Bottom wall 66 of outlet half 36 includes a recessed channel network 80 in fluid communication with fluid outlet passage 72. As illustrated in FIG. 2, recessed channel network 80 is radially symmetric about outlet opening 72. More specifically, recessed channel network 80 includes concentrically arranged circular channels 82 and 84, and a plurality of radially extending channels 86 intersecting with circular channels 82 and 84 and outlet passage 72. A plurality of radially extending channel segments 88 provide additional fluid communication between circular channels 82 and 84. It will be appreciated that channel network 80 enhances the present invention, whereby fluid pressure across the face of membrane filter 38 is more uniformly distributed.

In accordance with the principles of the present invention, fluid dispersion structure 60 is integrally molded with inlet half 34, and functions to radially disperse a stream of fluid entering filter chamber 78 through fluid inlet passage 50 along the longitudinal axis thereof. Referring to FIGS. 3 and 4, fluid dispersion structure 60 comprises a planar fluid-contacting plate member 90 and a plurality of circumferentially spaced support members 92. Support members 92 extend between bottom wall 44 and the peripheral edge of plate member 90 to support the plate member in parallel spaced relationship with the bottom wall. Plate member 90 has a concave fluid-contacting surface 94 facing bottom wall 44 in registry with fluid inlet passage 50 along the longitudinal axis thereof.

A primary advantage of filter capsule assembly 14, according to the present invention, is the ease by which inlet half 34 including fluid dispersion structure 60 is manufactured by injection molding without requiring inserts, cores, and the like. Specifically, structure 60 is designed so that the area of fluid-contacting surface 94 is no greater than the minimum transverse cross-sectional area of fluid inlet passage 50, thereby facilitating the use of a simple two-part molding die. Referring to FIG. 1, the shape of inner surface 52 defining fluid inlet passage 50 is preferably frustoconical, narrowing in cross-section in the direction of fluid flow into filter chamber 78. In the disclosed embodiment, opening 54 has the minimum transverse cross-sectional area of fluid inlet passage 50.

The foregoing description of the relationship between fluid-contacting surface 94 and fluid inlet passage 50, may also be expressed by noting that the area of fluid-contacting surface 94 is determined by the intersection of fluid-contacting surface 94 with an imaginary frustum defined by inner surface 52 extended toward plate member 90. For ease of mold release, the shape of inner surface 52 is frustoconical; however, the shape thereof may tend toward the practical limit of a cylinder.

Referring again to FIGS. 3 and 4, support members 92 extend from the periphery of fluid-contacting plate member 90 to inner surface 46 circumjacently along an imaginary cylinder defined by a projection of fluid-contacting surface 94 toward bottom wall 44 along the longitudinal axis of inlet passage 50. In other words, radially inwardly facing surfaces 96 of support members 92 are circumferentially spaced circumjacent fluid contacting surface 94 at their point of contact with plate member 90, and remain at least so spaced as they extend toward intersection with inner surface 46.

As will now be generally described, the filter capsule assembly according to the present invention is useful in preparing membrane filters for subsequent analysis by a particulate detection system, such as the Accumetric fuel contamination detector, manufactured by TMI of Fort Wayne, Ind. As previously described, the Accumetric fuel contamination detector utilizes two serially arranged membrane filters, e.g., membrane filters 38 and 40. However, filter capsule assembly 14 disclosed herein may also be used to prepare more than two or only one membrane filter for analysis.

Referring to FIG. 1, inlet half 34 and outlet half 36 are telescopingly engaged, with membrane filters 38 and 40 and support pad 42 retained in place. It will be noted that when the filter capsule is fully assembled, plate member 90 of dispersion structure 60 is spaced from the face of membrane filter 38, thereby ensuring that the entire surface of the membrane filter is exposed to fluid. Fully assembled filter capsule assembly 14 is then operably placed within outer enclosure assembly 12. Specifically, an end portion 98 of inlet pipe 22 is received within fluid inlet passage, while an O-ring 100 provides a seal between boss 58 and bottom wall 18 upon closure of enclosure assembly 12. Similarly, an O-ring 102 provides the wall of outlet port 28 and boss 7 inserted therein. O-rings 100 and 102 are preferably made of Nitrile rubber, or some other material appropriate to the type of fluid being sampled.

Once fuel monitor assembly 10 is operably assembled, inlet pipe 22 is connected to a source of fluid from which a fluid sample will be drawn through filter capsule assembly 14. Fluid entering end portion 98 axially through inlet passage 50 will impact fluid-contacting surface 94 of fluid dispersion structure 60, and will be radially dispersed through the spaces circumferentially intermediate support members 92. Where surface 94 has a concave shape, fluid will be directed somewhat toward inside surface 46. In this manner, a stream of fluid entering inlet passage 50 will not directly impact membrane filter 38, but will be radially dispersed so as to result in a more even fluid pressure across the face of the filter. Consequently a more uniform distribution of particulates on the membrane filter results.

It will be appreciated that inlet half 34 is preferably injection molded using Tenite thermoplastic molding composition, as manufactured by Eastman Chemical Products, Inc. of Kingsport, Tenn. However, other suitable thermoplastic molding compositions and materials may be used without departing from the spirit or scope of the present invention.

It will be appreciated that the foregoing description of a preferred embodiment of the invention is presented by way of illustration only and not by way of any limitation, and that various alternatives and modifications may be made to the illustrated embodiment without departing from the spirit and scope of the invention.

What is claimed is:

1. A filter capsule assembly through which a fluid sample is passed in order to filter off particulates suspended therein, wherein the particulates are subsequently analyzed to determine the particulate contamination level of the fluid sample, comprising:

an inlet half including an inlet bottom wall, a fluid inlet opening extending through said inlet bottom wall, and an inlet side wall extending upwardly from said inlet bottom wall, said fluid inlet opening extending along a longitudinal axis substantially normal to said inlet bottom wall and having along the axial length thereof a minimum transverse cross-sectional area;

an outlet half including an outlet bottom wall, a fluid outlet opening extending through said outlet bottom wall, and a generally cylindrical outlet side wall extending upwardly from said outlet bottom wall, said inlet half and said outlet half being adapted to engage one another to define a filter chamber bounded by said inlet and outlet bottom walls and said inlet and outlet side walls;

a filter element retained intermediate said inlet bottom wall and said outlet bottom wall within said filter chamber when said inlet half and said outlet half are engaged; and means for distributing said particulates on said element in a layer of substatially uniform thickness, including fluid dispersion means associated with said inlet half for radially dispersing a stream of fluid that would enter said filter chamber through said fluid inlet along said longitudinal axis, said fluid dispersion means comprising a fluid-contacting plate member and support means extending between said inlet bottom wall and the peripheral edge of said plate member for supporting said plate member in spaced relationship with said inlet bottom wall, said plate member having a fluid-contacting surface facing said inlet bottom wall in registry with said fluid inlet opening along said longitudinal axis, the area of said fluid-contacting surface being no greater than said minimum transverse cross-sectional area of said fluid inlet opening.

2. The filter capsule assembly of claim 1 in which:
said filter element comprises a planar microporous membrane disposed in a plane transverse to said longitudinal axis.

3. The filter capsule assembly of claim 1 in which:
said filter element comprises a pair of planar microporous membranes stacked adjacent one another and disposed in a plane transverse to said longitudinal axis.

4. The filter capsule assembly of claim 1 in which:
said outlet bottom wall includes a recessed channel network in fluid communication with said fluid outlet opening.

5. The filter capsule assembly of claim 4 in which:
said recessed channel network is radially symmetric about said fluid outlet opening.

6. The filter capsule assembly of claim 4 in which:
said recessed channel network includes a plurality of concentrically arranged circular channels and a plurality of radially extending channels intersecting with said plurality of circular channels.

7. The filter capsule assembly of claim 1 in which:
said fluid inlet opening is defined by an inner surface that is symmetric about said longitudinal axis, said inner surface being frustoconical, narrowing in cross-section in the direction of fluid flow into said filter chamber.

8. The filter capsule assembly of claim 7 in which:
said area of said fluid-contacting surface is determined by the intersection of said fluid-contacting surface with an imaginary frustum defined by said inner surface extended toward said plate member.

9. A filter capsule assembly through which a fluid sample is passed in order to filter off particulates suspended therein, wherein the particulates are subsequently analyzed to determine the particulate contamination level of the fluid sample, comprising:

a molded plastic cup-shaped inlet half including an inlet bottom wall, a fluid inlet opening extending through said inlet bottom wall at a central location thereof and being defined by an inner surface that is symmetric about a central longitudinal axis substantially normal to said inlet bottom wall, and a generally cylindrical inlet side wall extending upwardly from said inlet bottom wall coaxially about said longitudinal axis, said fluid inlet opening having along the axial length thereof a minimum transverse cross-sectional area;

a molded plastic, cup-shaped outlet half including an outlet bottom wall, a fluid outlet opening extending through said outlet bottom wall, and a generally cylindrical outlet side wall extending upwardly from said outlet bottom wall, said inlet half and said outlet half being adapted to selectively engage and disengage one another such that said inlet bottom wall and said outlet bottom wall inwardly face one another in spaced relationship and, together with said inlet side wall and said outlet side wall, define a filter chamber therebetween;

a planar filter element retained intermediate said inlet bottom wall and said outlet bottom wall within said filter chamber when said inlet half and said outlet half are selectively engaged, said filter element being disposed generally in a plane transverse to said longitudinal axis; and means for distributing said particulates on said element in a layer of substatially uniform thickness, including fluid dispersion means integrally molded with said inlet half for radially dispersing a stream of fluid that would enter said filter chamber through said fluid inlet along said longitudinal axis, said fluid dispersion means comprising a fluid-contacting plate member and a plurality of circumferentially spaced support members extending between said inlet bottom wall and the peripheral edge of said plate member to support said plate member in parallel spaced relationship with said inlet bottom wall, said plate member having a fluid-contacting surface facing said inlet bottom wall in registry with said fluid inlet opening along said longitudinal axis, the area of said fluid-contacting surface being no greater than said minimum transverse cross-sectional area of said fluid inlet opening.

10. The filter capsule assembly of claim 9 in which:
said planar filter element comprises at least one microporous membrane.

11. The filter capsule assembly of claim 9 in which:
said outlet bottom wall includes a recessed channel network in fluid communication with said fluid outlet opening.

12. The filter capsule assembly of claim 11 in which:
said recessed channel network is radially symmetric about said fluid outlet opening.

13. The filter capsule assembly of claim 11 in which:
said recessed channel network includes a plurality of concentrically arranged circular channels and a plurality of radially extending channels intersecting with said plurality of circular channels.

14. The filter capsule assembly of claim 9 in which:
said inner surface defining said fluid inlet opening is frustoconical, narrowing in cross-section in the direction of fluid flow into said filter chamber.

15. The filter capsule assembly of claim 14 in which:
said area of said fluid-contacting surface is determined by the intersection of said fluid-contacting surface with an imaginary frustum defined by said inner surface extended toward said plate member.

16. The filter capsule assembly of claim 9 in which:
said fluid-contacting surface is concave.

17. The filter capsule assembly of claim 9 in which:
said inlet side wall of said inlet half includes a top annular edge, the outer peripheral edge of said filter element being retained intermediate said top annular edge and said outlet bottom wall when said inlet half and said outlet half are engaged.

18. The filter capsule assembly of claim 9 in which:
said inlet side wall is frictionally telescopingly received within said outlet side wall.

19. The filter capsule assembly of claim 9 in which:
said plurality of support members extend from said fluid-contacting plate member to said inlet bottom surface circumjacent an imaginary cylinder defined by a projection of said fluid-contacting surface toward said inlet bottom surface along said longitudinal axis.

20. In a particulate detection system wherein a fluid sample containing particulates is passed through a filter in order to filter off the particulates for analysis and determination of the particulate contamination level of the fluid sample, a filter capsule assembly, comprising:
an inlet half including an inlet bottom wall, a fluid inlet opening extending through said inlet bottom wall, and an inlet side wall extending upwardly from said inlet bottom wall, said fluid inlet opening extending along a longitudinal axis substantially normal to said inlet bottom wall and having along the axial length thereof a minimum transverse cross-sectional area;
an outlet half including an outlet bottom wall, a fluid outlet opening extending through said outlet bottom wall, and a generally cylindrical outlet side wall extending upwardly from said outlet bottom wall, said outlet bottom wall including a recessed channel network in fluid communication with said fluid outlet opening, said inlet half and said outlet half being adapted to engage one another to define a filter chamber bounded by said inlet and outlet bottom walls and said inlet and outlet side walls;
a planar microporous filter element retained intermediate said inlet bottom wall and said outlet bottom wall within said filter chamber when said inlet half and said outlet half are engaged, said filter element being disposed generally in a plane normal to said longitudinal axis; and
means for distributing said particulates on said element in a layer of substatially uniform thickness, including fluid dispersion means associated with said inlet half for radially dispersing a stream of fluid that would enter said filter chamber through said fluid inlet along said longitudinal axis, said fluid dispersion means comprising a fluid-contacting plate member and a plurality of circumferentially spaced support members extending between said inlet bottom wall and the peripheral edge of said plate member to support said plate member in spaced relationship with said inlet bottom wall, said plate member having a fluid-contacting surface facing said inlet bottom wall in registry with said fluid inlet opening along said longitudinal axis, the area of said fluid-contacting surface being no greater than said minimum transverse cross-sectional area of said fluid inlet opening, and said plurality of support members being radially outside an imaginary cylinder generated by an axial projection of said fluid-contacting surface toward said fluid-contacting surface.

* * * * *